United States Patent
Cully et al.

(10) Patent No.: US 9,694,108 B2
(45) Date of Patent: Jul. 4, 2017

(54) MEDICAL DEVICE AMENEABLE TO FENESTRATION

(71) Applicant: W. L. Gore & Associates, Inc., Newark, DE (US)

(72) Inventors: Edward H. Cully, Flagstaff, AZ (US); Warren J. Cutright, Flagstaff, AZ (US); Craig T. Nordhausen, Parker, CO (US); Michael J. Vonesh, Flagstaff, AZ (US); James T. Walter, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 23 days.

(21) Appl. No.: 13/955,899

(22) Filed: Jul. 31, 2013

(65) Prior Publication Data

US 2013/0317601 A1    Nov. 28, 2013

Related U.S. Application Data

(63) Continuation of application No. 10/251,031, filed on Sep. 20, 2002, now abandoned.

(51) Int. Cl.
*A61F 2/06* (2013.01)
*A61L 27/50* (2006.01)
(Continued)

(52) U.S. Cl.
CPC ............. *A61L 27/507* (2013.01); *A61F 2/07* (2013.01); *A61B 17/3478* (2013.01); *A61F 2/89* (2013.01);
(Continued)

(58) Field of Classification Search
CPC ........ A61F 2/07; A61F 2/89; A61F 2002/072; A61F 2002/061; A61F 2002/821; A61F 2/852
(Continued)

(56) References Cited

U.S. PATENT DOCUMENTS

| 4,482,516 A | 11/1984 | Bowman et al. |
| 4,988,356 A | 1/1991 | Crittenden et al. |

(Continued)

FOREIGN PATENT DOCUMENTS

| WO | 99/60915 | 2/1999 |
| WO | 99/29262 | 6/1999 |
| WO | 99/39663 | 8/1999 |

OTHER PUBLICATIONS

Annecchino FL et al. "Palliative Reconstruction of the Right Ventricualr Outflow Tract in Tricuspid Atresia: A Report of 5 Patients." Ann Thor Surg 1980; 29(4) 317-21.
(Continued)

*Primary Examiner* — Katherine Rodjom

(57) ABSTRACT

The present invention is directed to a device that permits a permanent aperture to be formed in a wall, or other partition, of an implantable medical device. The present invention maintains the continuity and fluid-retaining properties of the implantable medical device by providing a breachable barrier material fully covering an opening delimited by a deformable framework. The invention is accessed with conventional interventional surgical instruments that disrupt and displace the barrier material. Following disruption of the barrier material, the opening is enlarged with surgical instruments to form a permanent framed aperture in the wall of the implantable medical device. The permanent framed aperture provides fluid communication across the wall of the implantable medical device.

36 Claims, 14 Drawing Sheets

(51) Int. Cl.
*A61F 2/07* (2013.01)
*A61B 17/34* (2006.01)
*A61F 2/82* (2013.01)
*A61F 2/89* (2013.01)

(52) U.S. Cl.
CPC ... *A61F 2002/061* (2013.01); *A61F 2002/065* (2013.01); *A61F 2002/072* (2013.01); *A61F 2002/075* (2013.01); *A61F 2002/821* (2013.01); *A61F 2220/005* (2013.01); *A61F 2220/0058* (2013.01); *A61F 2220/0075* (2013.01)

(58) Field of Classification Search
USPC .................. 623/1.11, 1.12, 1.16, 1.32, 1.35
See application file for complete search history.

(56) References Cited

U.S. PATENT DOCUMENTS

| | | | |
|---|---|---|---|
| 5,102,403 A | 4/1992 | Alt | |
| 5,135,535 A | 8/1992 | Kramer | |
| 5,171,222 A | 12/1992 | Euteneuer et al. | |
| 5,195,978 A | 3/1993 | Schiffer | |
| 5,205,822 A | 4/1993 | Johnson et al. | |
| 5,324,269 A | 6/1994 | Miraki | |
| 5,334,147 A | 8/1994 | Johnson | |
| 5,336,184 A | 8/1994 | Teirstein | |
| 5,380,283 A | 1/1995 | Johnson | |
| 5,389,087 A | 2/1995 | Miraki | |
| 5,395,335 A | 3/1995 | Jang | |
| 5,472,425 A | 12/1995 | Teirstein | |
| 5,476,589 A | 12/1995 | Bacino | |
| 5,489,271 A | 2/1996 | Andersen | |
| 5,549,663 A * | 8/1996 | Cottone, Jr. | A61F 2/07 606/195 |
| 5,683,448 A | 11/1997 | Cragg | |
| 5,807,355 A | 9/1998 | Ramzipoor et al. | |
| 5,824,043 A | 10/1998 | Cottone | |
| 5,919,164 A | 7/1999 | Andersen | |
| 5,993,489 A | 11/1999 | Lewis et al. | |
| 6,071,307 A | 6/2000 | Rhee | |
| 6,095,990 A | 8/2000 | Parodi | |
| 6,187,035 B1 * | 2/2001 | Jang | A61F 2/91 623/1.15 |
| 6,245,100 B1 | 6/2001 | Davila et al. | |
| 6,299,595 B1 | 10/2001 | Dutta et al. | |
| 6,327,772 B1 | 12/2001 | Zadno-Azizi et al. | |
| 6,331,191 B1 * | 12/2001 | Chobotov | A61F 2/07 623/1.21 |
| 6,355,056 B1 | 3/2002 | Pinheiro | |
| 6,395,018 B1 | 5/2002 | Castaneda | |
| 6,398,799 B2 | 6/2002 | Kramer | |
| 6,398,803 B1 | 6/2002 | Layne et al. | |
| 6,428,565 B1 | 8/2002 | Wisselink | |
| 6,432,127 B1 * | 8/2002 | Kim et al. | 623/1.11 |
| 6,511,505 B2 | 1/2003 | Cox et al. | |
| 6,579,314 B1 | 6/2003 | Lombardi et al. | |
| 6,599,315 B2 | 7/2003 | Wilson | |
| 6,673,103 B1 * | 1/2004 | Golds et al. | 623/1.13 |
| 6,835,203 B1 | 12/2004 | Vardi et al. | |
| 6,896,694 B1 | 5/2005 | Filho et al. | |
| 2002/0193872 A1 * | 12/2002 | Trout, III | A61F 2/07 623/1.34 |
| 2003/0130720 A1 | 7/2003 | De Palma et al. | |
| 2004/0054403 A1 | 3/2004 | Israel | |

OTHER PUBLICATIONS

Bridges ND et al. "Effect of Baffle Fenestration on Outcome of the Modified Fontan Operation" Circulation 1992; 86:1762-69.
Fontan F et al. "Correction de l'atresie tricuspidienne." ["Correction" of tricuspid atresia. 2 cases "corrected" using a new surgical technique.] Ann Chir Thorac Cardiovasc 1971; 10:39-47.
Glenn WL et al. "Rational Approach to the Surgical Management of Tricuspid Atresia" Circulation 1968; 37:1162-67.
Ottenkamp JAAP et al. "Nine years' experience of physiological correction of tricuspid atresia: long-term results and current surgical approach." Thorax 1982; 37:718-726.
Parodi J.C., Palmaz JC, Barone HD "Transfemoral Intraluminal Graft Implantation for Abdominal Aortic Aneurysms." Ann Vasc Surg 1991; 5:491-9.
Schatz RA et al. "Balloon-expandable intracoronary stents in the adult dog." Circulation 1987; 76{2}:450-457.
International Preliminary Examination Report from PCT/US2003/029200, completed Dec. 2, 2004, 4 pages.

* cited by examiner

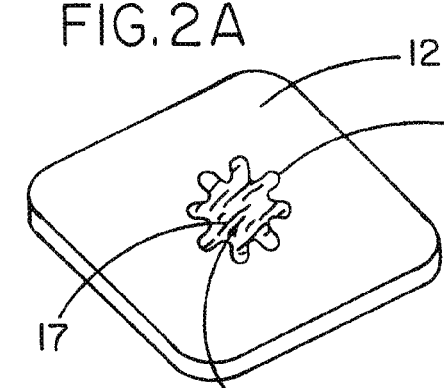
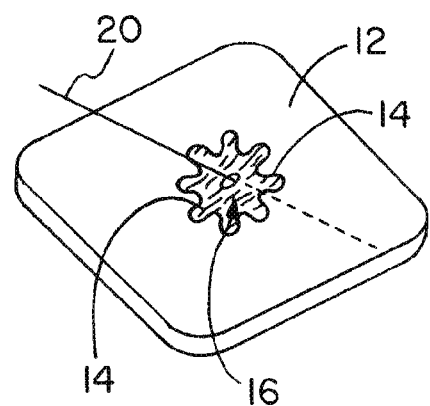
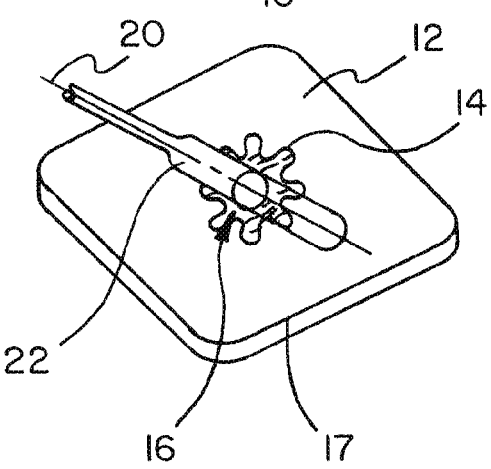
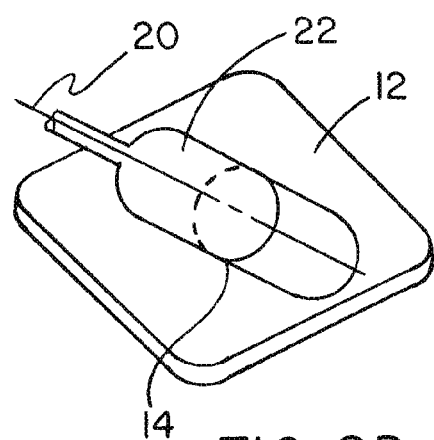
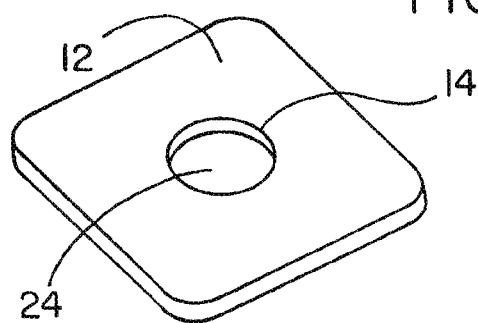

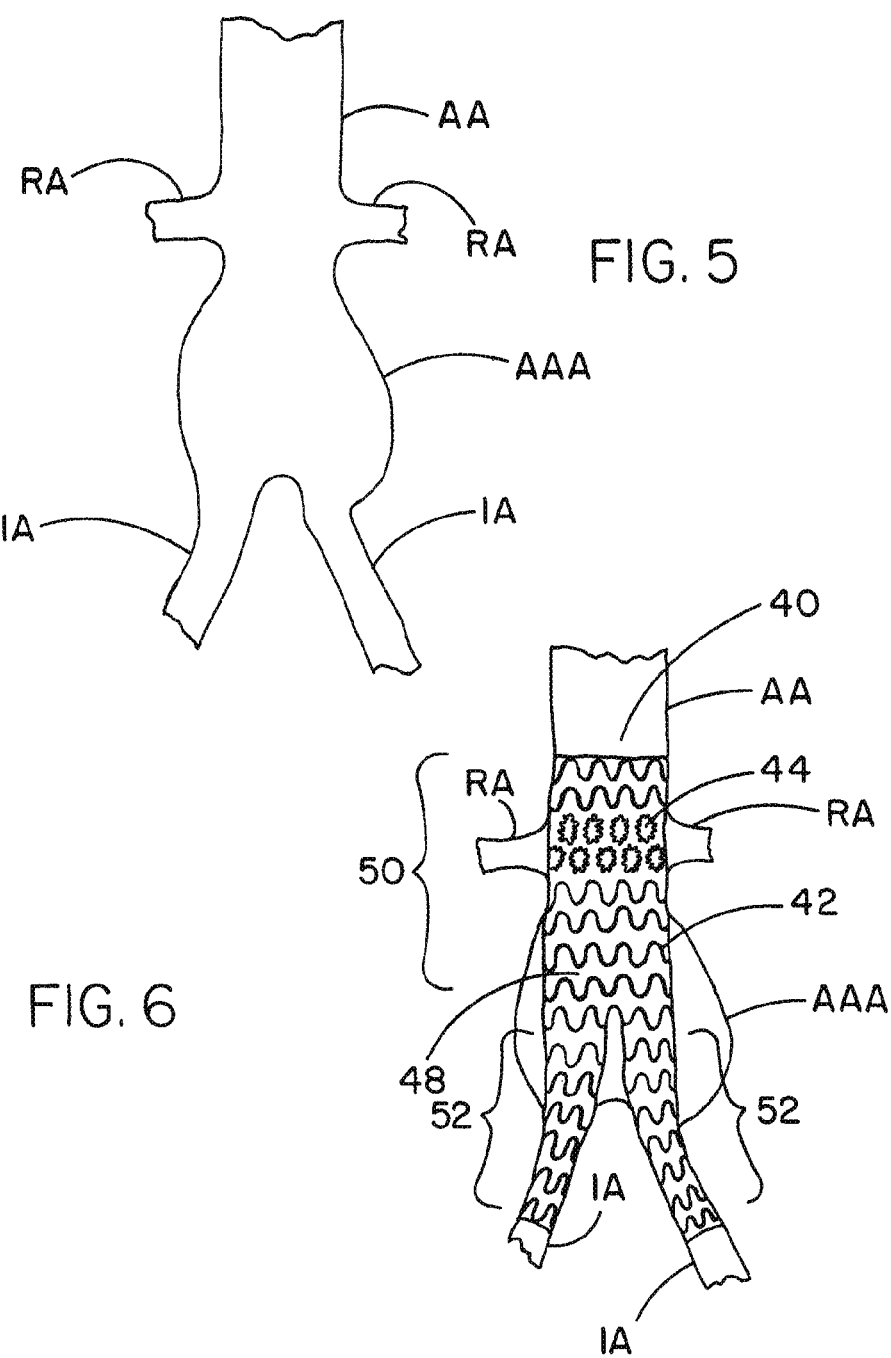

MEDICAL DEVICE AMENEABLE TO FENESTRATION

CROSS-REFERENCE TO RELATED APPLICATIONS

This application is a continuation of U.S. patent application Ser. No. 10/251,031, now abandoned, entitled "Medical Device Amenable To Fenestration", the content of which is hereby incorporated by reference in its entirety.

FIELD OF THE INVENTION

The present invention relates to implantable medical devices. More particularly, the invention relates to means for forming a framed aperture in wall portions, or other partitions, of implantable medical devices to establish and maintain fluid communication across the wall portion of the medical device. The present invention also relates to methods of making the invention.

BACKGROUND OF THE INVENTION

Abdominal aortic aneurysms (AAAs) and thoracic aortic aneurysms (TAAs) are diagnosed in approximately 250,000 and 20,000 patients respectively each year. Left untreated, these aneurysms commonly progress to rupture resulting in death. Prior to the advent of interventional catheter-based techniques, conventional surgical treatment has been the method of treatment for these lesions. Due to the often emergent condition of these patients and the potential for significant blood loss, high morbidity and mortality rates have been associated with this type of surgery.

With the introduction of catheter-based interventional techniques, new non-surgical therapies were made available to many patients. Since the initial animal work performed by Schatz et. al., small metallic tubes (i.e., stents) have been found to be of significant benefit for patients with coronary artery and peripheral artery disease. Schatz, R. A., Palmaz, J. C., Tio, F. O., Garcia, F., Garcia, O., Reuter, S. R. "Balloon-expandable intracoronary stents in the adult dog." *Circulation* 76:450-7 (1987). In an effort to treat abdominal aortic aneurysms, Parodi et. al. reported on their experience with combining the barrier properties of synthetic vascular grafts with stent technology (i.e., stent-graft) to effectively inhibit blood flow into the aneurysm sac using catheter delivery systems. Parodi, J. C., Palmaz, J. C., Barone, H. D. "Transfemoral intraluminal graft implantation for abdominal aortic aneurysms." *Ann. Vasc. Surg* 5:491-9 (1991).

This technology has continued to progress with significant improvements in successful device deployment and improved patient outcomes. Despite these improvements, there are many patients for which this technology is not applicable as a result of unique anatomical or disease conditions. Specifically, in the case of AAA disease, stent-graft devices typically require some amount of healthy vessel both proximal and distal to the aneurysm sac into which to place the stent-graft. In many patients, the proximal vessel is not long enough to achieve adequate fixation. Placement of the stent-graft in a more proximal location in these patients in order to achieve adequate fixation could partially or completely occlude the renal arteries providing blood to the kidneys. A number of different device designs have been proposed to allow device fixation to the aortic vessel proximal to the renal arteries (i.e., suprarenal fixation). Widespread applicability of supra-renal fixation devices has been limited by the flexibility of these designs, morphological variation of aneurysmal neck geometry across patients, and the coverage of the renal ostia with metallic stents which can act as a nidus for thromo-embolism of the renal circulation and/or hinder subsequent interventional access to this vasculature.

A similar situation exists for TAA disease. These aneurysmal lesions are often located in close proximity to the subclavian and carotid arterial branches. When inadequate proximal vascular tissue is available for anchoring the endoprosthesis, a suitable proximal anchoring zone can be created by performing a surgical transposition prior to the interventional procedure. This surgical approach is intended to assure continued flow to all vessels. Alternative means for achieving side-branch perfusion through the wall of a stent-graft are therefore desirable.

Other clinical conditions where there would be a benefit for fluid communication through the wall of a prosthesis are those involving cardiac surgery. Arterial blood leaving the heart serves to carry oxygen to the body. In contrast, venous blood is returned to the heart via the superior and inferior vena cava after releasing oxygen to the body and absorbing carbon dioxide and other waste products. Approximately 40,000 children are born each year with congenital heart defects. These abnormalities often involve a single functional ventricle and defects in the tissues (i.e., septum) separating the right (venous) and left (arterial) side of the heart. Mixing of arterial and venous blood in these patients results in reduced oxygen carrying capacity and often shortened life expectancies.

Cardiac surgical interventions performed for the most complex congenital heart abnormalities often require multiple surgical procedures to effect the final treatment for the patient. The Fontan procedure is an example of a staged surgical treatment that is designed to overcome these significant structural heart abnormalities and isolate systemic and pulmonary circulation at the definitive treatment. "Correction de l'atresie tricuspidienne." Fontan, F., Mounicot, F. B., Baudet, E., Simonneau, J, Gordo, J., Gouffrant, J. M. Rapport de deux cas "corriges" par l'utilisation d'une technique chirurgicale nouvelle. ["Correction" of tricuspid atresia. 2 cases "corrected" using a new surgical technic] *Ann-Chir-Thorac-Cardiovasc* 10:39-47 (1971). Annecchino, F. P., Fontan, F., Chauve, A., Quaegebeur, J. "Palliative reconstruction of the right ventricular outflow tract in tricuspid atresia: a report of 5 patients." *Ann-Thorac-Surg.* 29:317-21 (1980). Ottenkamp, J., Rohmer, J., Quaegebeur, J. M., Brom, A. G., Fontan, F. "Nine years' experience of physiological correction of tricuspid atresia: long-term results and current surgical approach." *Thorax* 37:718-26 (1982). The surgical procedures must be staged to minimize the pressure and volume loads on the remaining functional single ventricle. In the first stage procedure, a connection is created between the Superior Vena Cava (SVC) and the Pulmonary Artery (PA). This is referred to as a Hemi-Fontan or Glenn Shunt procedure. Mathur, M., Glenn, W. W. "Rational approach to the surgical management of tricuspid atresia." *Circulation* 37:1162-7 (1968). This shunt reduces the degree of venous and arterial blood mixing, and improves oxygenation of the blood.

Once the pulmonary circulation and functional ventricle are sufficiently developed, a subsequent procedure is performed wherein the blood going to the right ventricle is bypassed by routing the blood in the Inferior Vena Cava (IVC) directly to the PA by way of a baffle or tube connecting the IVC to the PA. At the time of this procedure, a small hole is typically created in the side of the connection tube to allow some flow of blood into the right ventricle. This small hole is considered a temporary connection that reduces the work for the remaining ventricle when pulmonary vascular resistance is elevated. Bridges, N. D., Mayer, J. E., Lock, J. E., Jonas, R. A., Hanley, F. L., Keane, J. F., Perry, S. B., Castaneda, A. R. "Effect of baffle fenestration on outcome of the modified Fontan operation." *Circulation* 86:1762-9 (1992).

The final surgical procedure involves either surgical closure or transcatheter occlusion of the temporary hole in the IVC to PA connector tube. This multi-staged conventional surgical approach for patients with complex congenital heart disease is not optimal as it puts patients at additional risk of morbidity and mortality with each subsequent surgical intervention. This risk may be reduced if the first surgical intervention can set the stage for a future minimally invasive procedure that eliminates the need for additional open-heart surgery.

Various devices and design modifications have been proposed in an effort to provide access to anatomical structures surrounding the device or to internal spaces of the device.

U.S. Pat. No. 6,428,565, issued to Wisselink, and U.S. Pat. No. 6,395,018, issued to Castaneda, each relate to stent-graft systems with pre-formed apertures to allow for side-branch access. Neither of these devices have apertures that are closed at the time of initial implant.

U.S. Pat. No. 6,398,803, issued to Layne, et. al., relates to partially covered stents having various patterns of open apertures along the length of the device. As with the Wisselink and Castaneda devices, the apertures are fully formed prior to deployment of the device.

U.S. Pat. No. 6,432,127, issued to Kim, et. al., discloses formation of an aperture in the wall of a vascular conduit through the use of a cutting tool. The conduit does not provide a deformable framework encompassing the aperture formation site. As a result, targeting the precise location of the region in which to create the aperture is difficult to visualize using conventional imaging techniques. Moreover, the aperture is not reinforced along its peripheral regions once the aperture is formed. The absence of a framework delimiting the aperture formation site precludes precise sizing of the aperture during its formation.

There remains a need for a device that initially maintains the continuity and fluid-retaining properties of a wall portion of an implantable medical device, while providing means for forming a permanent aperture in the medical device. Such a device would permit custom sizing of the aperture in situ at the implant site during surgery.

SUMMARY OF THE INVENTION

The present invention is directed to a device that is amenable to transmural fenestration. In particular, the present invention permits a permanent framed aperture to be formed in a wall, or similar partition, of implantable medical devices as a means for establishing and maintaining fluid communication across the wall of the medical device following implantation. The present invention provides a breachable barrier material that initially maintains the continuity and any fluid-retaining properties of the wall of the medical device. The breachable barrier material fully covers an opening delimited by a framework. In use, the breachable barrier material is breached with a surgical instrument and the shape of the framework altered to enlarge, or otherwise alter, the area of the opening. In the process, the opening becomes uncovered and accessible to flow of fluid through the opening. The altered framework provides structural reinforcement to peripheral regions (e.g., circumferential) of the enlarged opening and forms a permanent aperture in the wall of the medical device. The altered framework can also be used to provide a secure anchoring site for ancillary medical devices. The permanent aperture can be formed in the wall of the implantable medical device at the time of surgical or catheter-based intervention or at a later date through the use of interventional or surgical techniques.

The present invention is particularly suited for use with vascular prostheses, and other implantable medical devices providing fluid containment or fluid partitioning, that can benefit from the formation of one or more permanent apertures in the devices at the implantation site. With stent-grafts spanning an aneurysm, for example, the invention can provide a framed aperture in the wall of the stent-graft for side-branches or drainage sites. Vascular grafts can be bypassed or bifurcated in-situ with the present invention. The invention can also be used with surgically implanted cardiovascular patches to provide perfusion or other access to the heart and vascular system.

The present invention can be added to an implantable medical device following its construction, or included in the manufacture of the device as an integral component. The breachable barrier material of the present invention is made of implantable polymers that are readily breached, perforated, or otherwise structurally disrupted with surgical instruments. The breachable barrier material can also be made of polymers that are structurally disrupted through degradation and absorption by the body of the implant recipient. The polymers of the breachable barrier material can be incorporated with filler materials to assist in breaching the barrier material or to facilitate visualization of the aperture region in an implant recipient.

The framework is made of implantable metallic or polymeric materials that can be altered in shape. These framework materials can be deformed or otherwise altered in shape with surgical instruments or have shape-memory properties that permit the framework to assume different shapes without the use of an instrument. The framework materials are shaped in various ways to assist in the combined roles of structurally reinforcing the breachable barrier material and the opening, being capable of reconfiguration, and providing a permanent framed aperture.

In one surgical method, an implantable medical device utilizing the present invention is placed at a surgical site with conventional or interventional surgical techniques. Once the correct position of the medical device is confirmed, a catheter guide-wire, or other surgical instrument, is used to breach the breachable barrier material and begin to uncover the covered opening. An expandable balloon catheter in a deflated configuration is then inserted into the partially uncovered opening and inflated. As the balloon catheter is inflated, it expands in diameter, altering the shape of the framework and displacing the remaining barrier material from the area of the opening. When the framework has been reconfigured as desired, the balloon catheter is deflated and removed from the opening. This leaves a permanent framed aperture in the wall of the medical device. The permanent aperture can provide immediate therapies and surgical remedies, such as branch vessel perfusion, or co-operate with other medical devices.

In one embodiment, the present invention is an implantable medical device comprising a framework delimiting an opening having a first area and a breachable barrier material fully covering said opening, wherein a permanent aperture having a second area is formed following breach of said breachable material and said framework is adaptable to be altered in shape.

In another embodiment, the present invention is an implantable medical device comprising a continuous wall, at least one framework in said wall delimiting an opening having a first area, a breachable barrier material fully covering said opening, wherein a permanent aperture having a second area is formed following breach of said breachable material and said framework is adaptable to be altered in shape and have a reinforced peripheral region in said continuous wall.

Further aspects and advantages of the present invention will be apparent to those skilled in the art after reading and understanding the detailed description of preferred embodiments set forth hereinbelow and after viewing the accompanying drawings.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment that is presently preferred. It should be understood, however, that the invention is not limited to the precise arrangement and instrumentality shown. In the drawings:

FIGS. 2A-2E illustrate the present invention in operation.

FIG. 5 illustrates an abdominal aortic aneurysm.

FIG. 6 illustrates a stent-graft incorporating an embodiment of the present invention placed in the region of an abdominal aortic aneurysm.

The accompanying diagrams include various anatomical structures and associated clinical pathologies that are identified as follows:

AA=Abdominal Aorta
RA=Renal Artery
IA=Iliac Artery
AAA=Abdominal Aortic Aneurysm

DETAILED DESCRIPTION OF THE INVENTION

The present invention can be used in combination with a variety of implantable fluid-containing medical devices to establish fluid communication across a wall, or other partition, in the devices. In many situations, the present invention is employed at the time the medical device is implanted. In other instances, the present invention is accessed and utilized after the medical device has been implanted for a period of time. The present invention can also be used before the implant procedure begins.

Figure 1A:
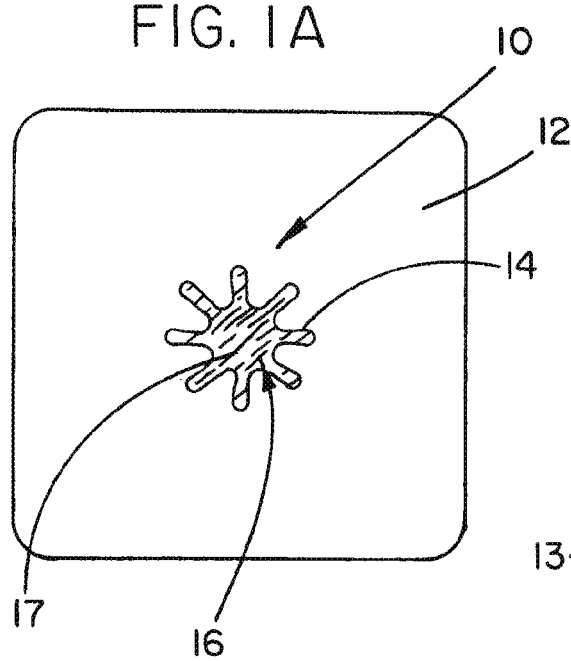
FIG. 1A illustrates a top view of the present invention.
Figure 1B:
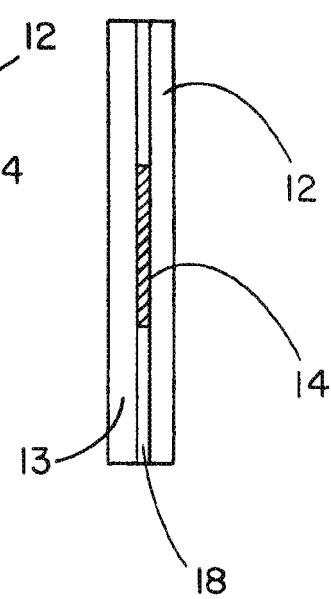
FIGS. 1B-1D illustrate a side view of the present invention.
Figure 1C:
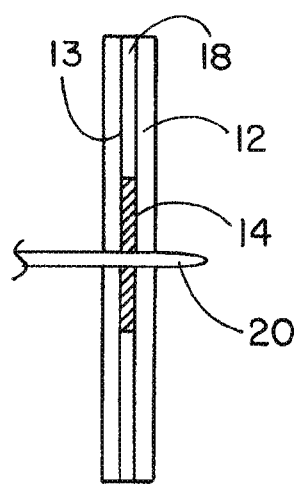
Figure 1D:
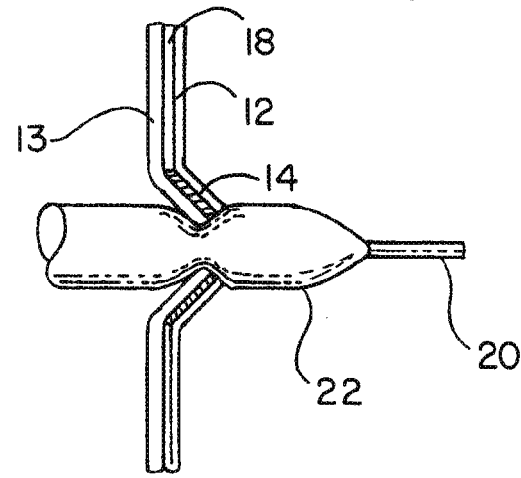

FIG. 1A is a top view of an embodiment of the present invention 10 incorporated into an implantable patch material 12. FIG. 1B is a side view of this embodiment generally illustrating the relationship of the components. In this embodiment, a framework 14 is surrounded by a layer of implantable polymeric material 18. The framework 14 delimits an opening 16 that is fully covered with a breachable barrier material 17. The polymer layer 18 is sandwiched between two layers of implantable patch material 12, 13 so as to reveal the framework 14, opening 16, and breachable barrier material 17 of the present invention. In similar embodiments of the present invention, the implantable patch material or other wall components are considered part of the invention. In addition to implantable medical devices having planar configurations, implantable medical devices having tubular configurations are also suitable for use with the present invention. Tubular medical devices are generally cylindrical in shape and not confined to having parallel walls. In addition, tubular medical devices have geometries with at least one inlet and at least one outlet.

Figure 8A:
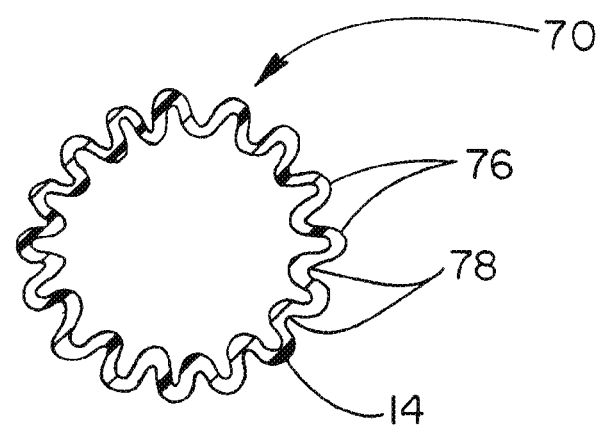
FIGS. 8A-8C illustrate the framework component of the present invention in various non-limiting shapes.
Figure 8B:
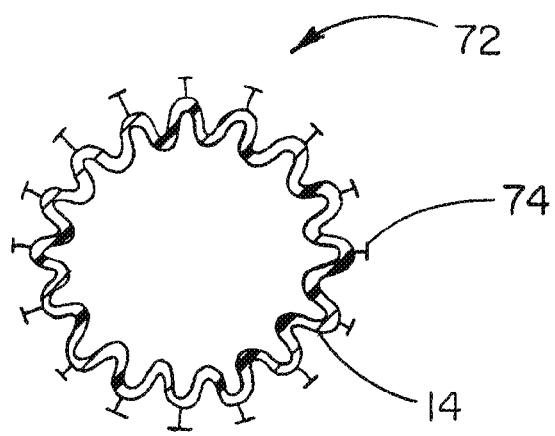
Figure 8C:
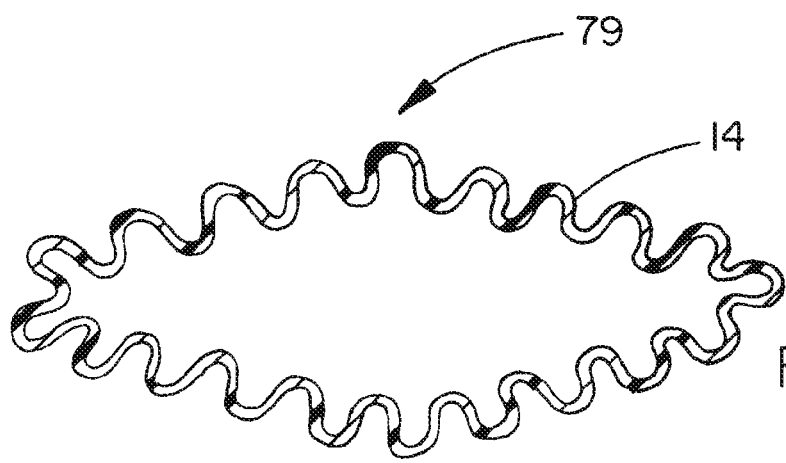
Figure 9:
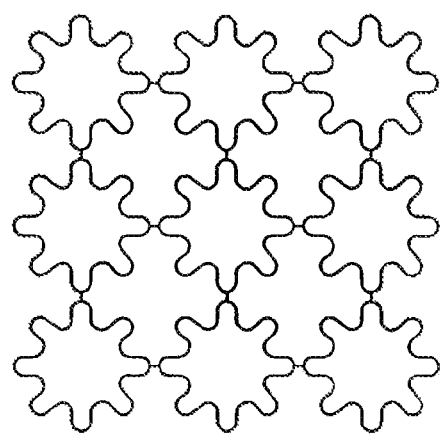
FIG. 9 illustrates the framework component of the present invention in the form of an array.
Figure 10:
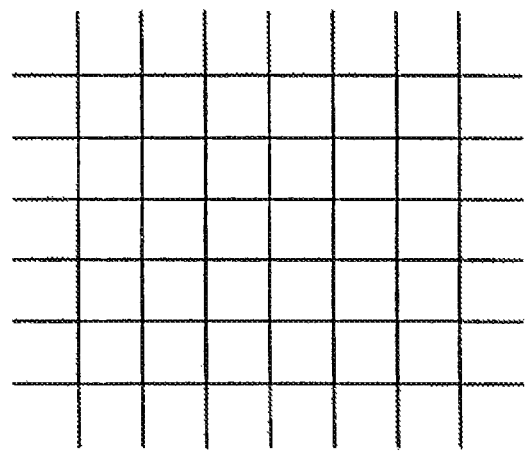
FIG. 10 illustrates the framework component of the present invention in the form of an array.

The shape of the framework 14 is chosen to provide structural support to the breachable barrier material 17 while it fully covers opening 16. The shape and composition of the framework also allows the framework to be readily deformed and displaced to peripheral regions of the opening to form a permanent framed aperture. The particular shape of the framework illustrated in FIG. 1A, et. al., is preferred but not limiting. For example, FIGS. 8B and 8C illustrate frameworks having circular configurations 70 incorporating varying numbers of peaks 76 and valleys 78. It is also contemplated in the present invention that the distance between the peaks 76 and valleys 78 (i.e., amplitude) can be varied broadly, thereby enabling a wide range of framework geometries to be formed. In addition to enhancing support for the breachable barrier material with these framework designs, a wide range of aperture sizes can be achieved with these designs. Supporting leg struts 74 can also be incorporated into the framework design to enhance attachment to surrounding wall materials. Other non-circular configurations 79 of the framework 14 are also contemplated. Furthermore, FIGS. 9 and 10 illustrate that the framework can be in the form of an array of openings. These embodiments provide a choice of locations for the framed aperture as well as the number of framed apertures.

FIGS. 2A-2E illustrate the construct of FIGS. 1A and 1B in use. FIG. 2A is a perspective view of the construct as it might appear at an implantation site. FIG. 2B shows a guide wire 20 from a catheter, or other device, having penetrated and breached the breachable barrier material 17. FIG. 2C depicts an expandable balloon catheter 22 in a deflated state being introduced through the breached barrier material into opening 16 with guide wire 20. FIG. 2D illustrates inflation of the expandable balloon catheter 22 and deformation of framework 14. As the framework 14 is deformed, opening 16 is enlarged and expanded in area. Following deflation and removal of the balloon catheter, FIG. 2E shows the resulting permanent aperture 24 framed with altered framework 14 in implantable patch material 12.

Figure 3A:
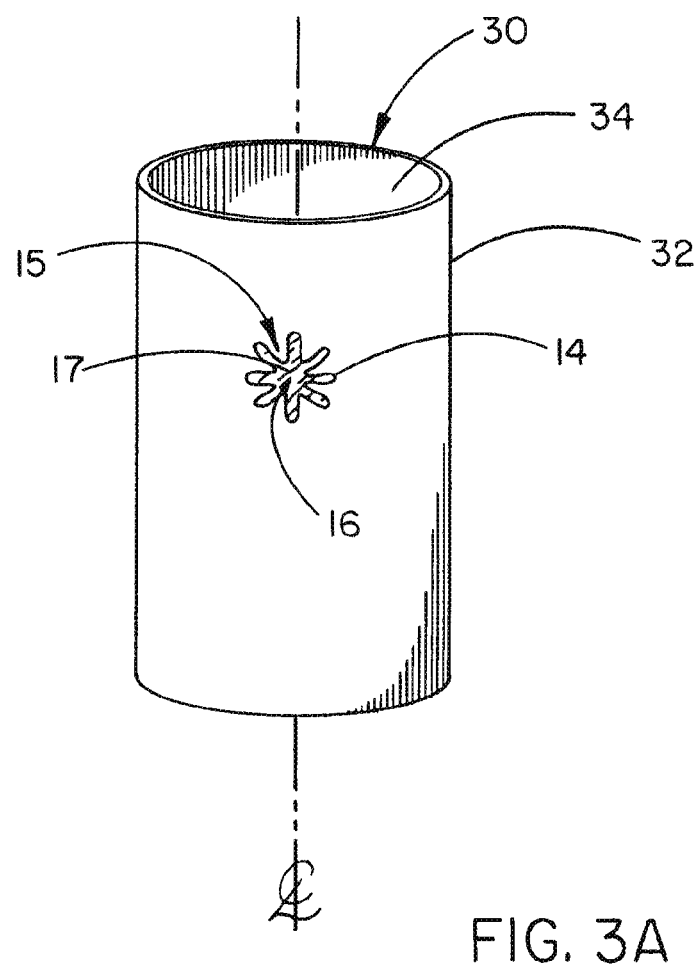
FIG. 3A illustrates an embodiment of the present invention incorporated into a wall of a tubular medical device.

FIG. 3A illustrates the present invention 15 as a component of a tubular vascular graft 30. In this embodiment, framework 14 delimiting opening 16 is fully covered by breachable barrier material 17 and incorporated into wall portion 32 of vascular graft 30. When the invention is operated, fluid communication across wall portion 32 to luminal space 34 is established.

Figure 3B:
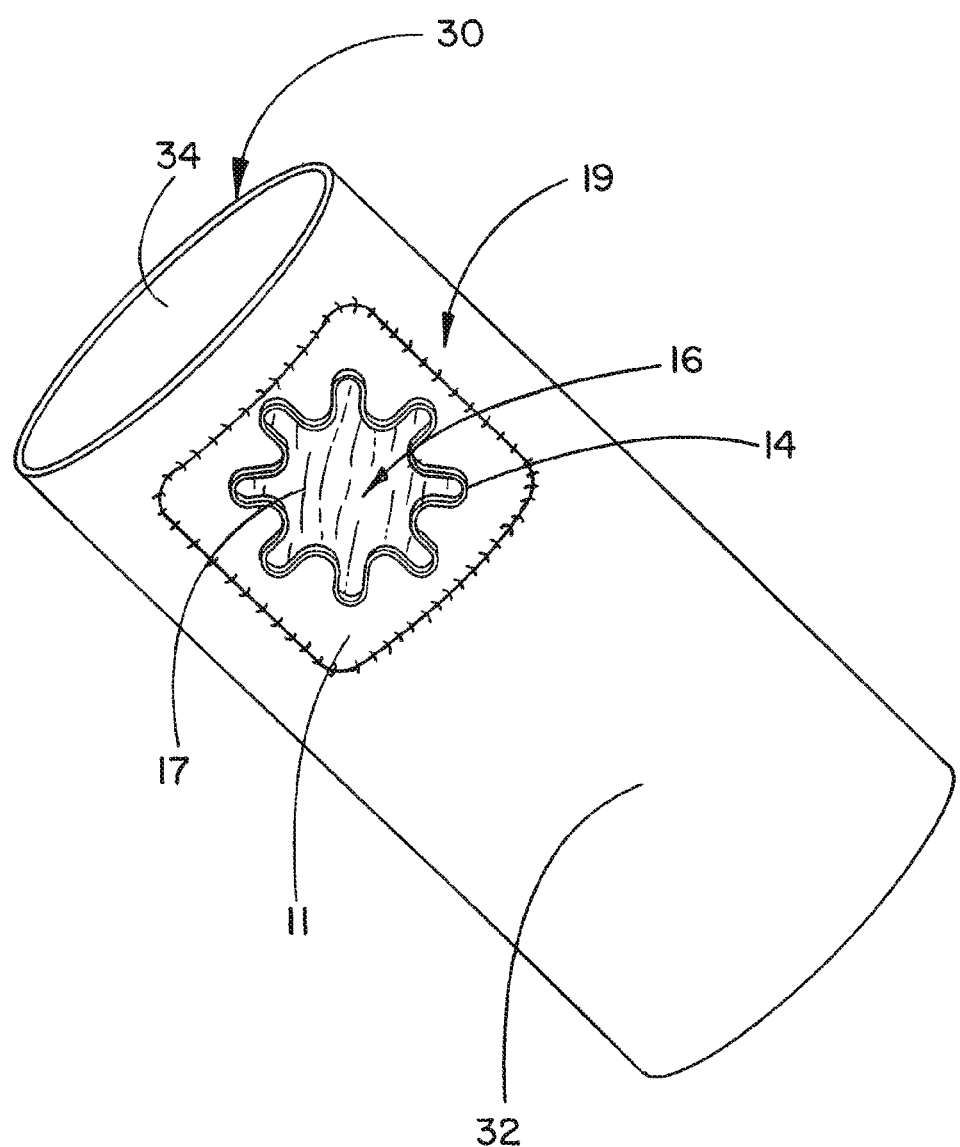
FIG. 3B illustrates an embodiment of the present invention incorporated into a planar material that is attached to a wall of a tubular medical device.

FIG. 3B illustrates an embodiment of the present invention 19 having an implantable patch material 11 component. The implantable patch material is attached to an implantable vascular prosthesis 30 by sewing. Other suitable means of attaching the present invention to a wall of an implantable medical device include, but are not limited to, adhering, ultrasonic or radio frequency welding, lamination, stapling, and covering the medical device with a membrane or film to include the present invention.

Figure 4:
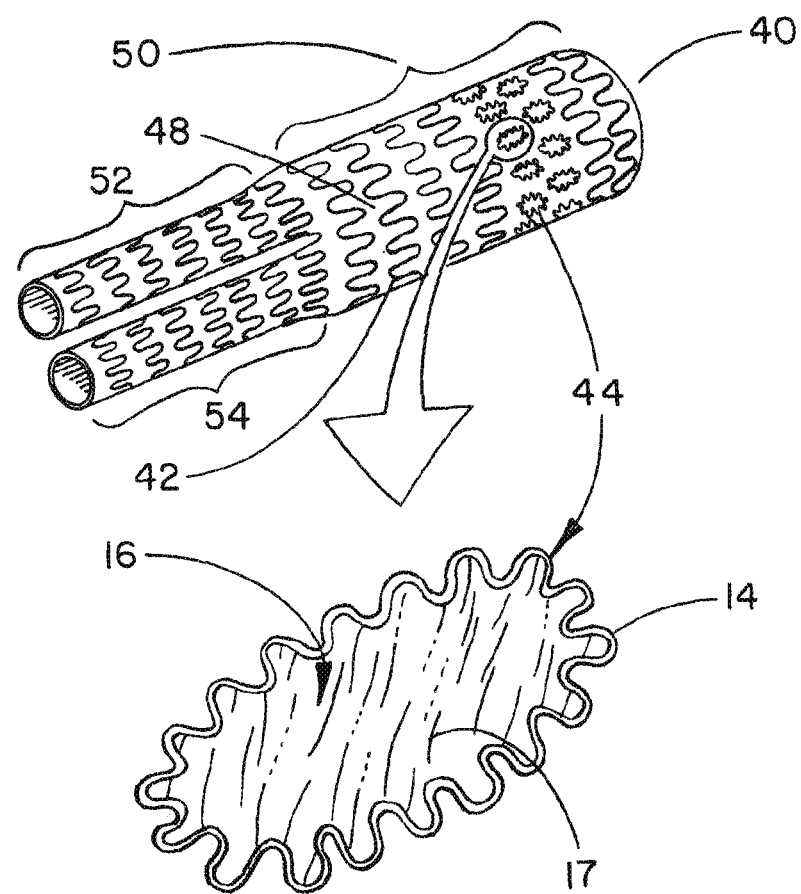
FIG. 4 illustrates an embodiment of the present invention incorporated into a medical device.

FIG. 4 illustrates an embodiment of the present invention 44 incorporated into an implantable tubular endovascular device 40. In this embodiment, the endovascular device 40 is a bifurcated design commonly used to treat aortic aneurysms and includes a main body, or trunk, portion 50 and two leg portions 52, 54. The endovascular device has a stent frame 42 and wall means 48. Several fully covered framework elements of the present invention are incorporated into the wall means 48 of the stent-graft 40. As seen in FIG. 4, there is a longitudinal displacement between the present invention and the support elements (i.e., scaffolding) of the stent-graft. This embodiment of the present invention provides multiple sites for forming side branches in stent-grafts and other endovascular devices as means for providing selective perfusion and/or drainage of the implantation site.

Figure 4A:
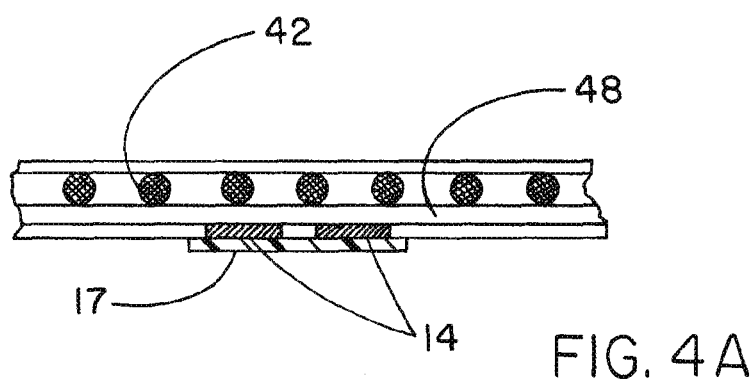
FIG. 4A illustrates an embodiment of the present invention placed in a discrete location relative to scaffolding and wall elements of an implantable medical device.

In embodiments of the present invention used in combination with stent-grafts, and other implantable medical devices utilizing support elements (i.e., scaffolding), the framework component of the present invention is preferably incorporated into the device separately from the support elements. As shown in FIG. 4A, the framework of the present invention underlies and is discrete from the support elements of the implantable medical device. The location of the present invention is not limited to contact or close proximity to support elements or wall components of an implantable medical device. Indeed, the present invention can be positioned in any desired location in an implantable medical device.

A clinical application of the embodiment illustrated in FIG. 4 is depicted in FIGS. 5 and 6. A typical abdominal aortic aneurysm (AAA) is shown in FIG. 5 with the proximal aorta (AA) leading to renal artery (RA) branches and distal iliac arteries (IAs). In cases where the disease condition or aortic anatomy does not provide sufficient healthy vessel upon which to achieve device fixation at implant, it is often necessary to utilize the AA segment proximal to the RAs. In this suprarenal implant position, an appropriate stent-graft 40 fixation can be achieved and effective AAA exclusion as shown in FIG. 6. In this configuration however, the barrier properties of the stent-graft wall 48 occlude blood flow to the branching RA on both sides. In order to achieve RA perfusion, one or more units 44 of the present invention are selected and utilized.

The interventional procedure required to access and operate the present invention is illustrated in FIGS. 7A-7D. Following deployment of stent graft 40, a guide catheter 36 is positioned under fluoroscopic guidance to direct a guide-wire 20 toward the center of one of the plurality of available inventions 44 that is in appropriate alignment with the RA. Following guide-wire 20 breach of the breachable barrier material 16, the framework 14 is altered in shape to the desired aperture size using a balloon catheter 22. Further inflation of the balloon 22 achieves the desired deformation of the framework 14 and formation of a permanent framed aperture 64 having a size appropriate for the RA. Once formed, the permanent framed aperture 64 provides for RA blood perfusion 62 in accordance with normal AA blood flow 60.

The present invention can be constructed of a variety of implantable materials. The breachable barrier material has a composition, structure, and/or thickness sufficient to at least partially bar liquids, including blood and other physiological fluids, from crossing the material, yet have sufficient structural weakness to be readily breached, perforated, or otherwise structurally disrupted with surgical instruments, or the like. The breachable barrier material can be made of non-biodegradable polymers, bio-degradable polymers, and elastomers, either alone or in combination. Elastomers in the breachable barrier materials can augment uncovering of the fully covered opening following breach of the barrier material. The breachable barrier material can be provided with filler materials that also augment breaching of the barrier material or assist in locating the invention at an implantation site.

Suitable surgical instruments or tools for use in breaching the barrier material at an implantation site include, but are not limited to, guide-wires, Colapinto® needles, Rotablators®, and other ablation instruments utilizing radio-frequency energy, ultrasonic sound, microwave energy, or laser light.

Suitable non-biodegradable polymers include, but are not limited to, polyester, polytetrafluoroethylene, polyamide, and polyurethane. The preferred material for the breachable barrier material is a porous expanded, or stretched, polytetrafluoroethylene material. Suitable bio-degradable polymers include, but are not limited to, materials made of polymers or copolymers possessing one or more of the following monomeric components: glycolide (glycolic acid); lactide (d-lactide, l-lactide, d,l-lactide); trimethylene carbonate; p-dioxanone; caprolactone, and hydroxybutyrate, hydroxyvalerate. Elastomeric materials suitable for use in the present invention include, but are not limited to, fluoroelastomers, polyurethane. Suitable filler materials for incorporation into the breachable barrier material include, but are not limited to, graphite, titanium oxide (TiO), barium, vitamin E, gadolinium, lossy materials, and other radio-opaque compositions.

Figure 11:
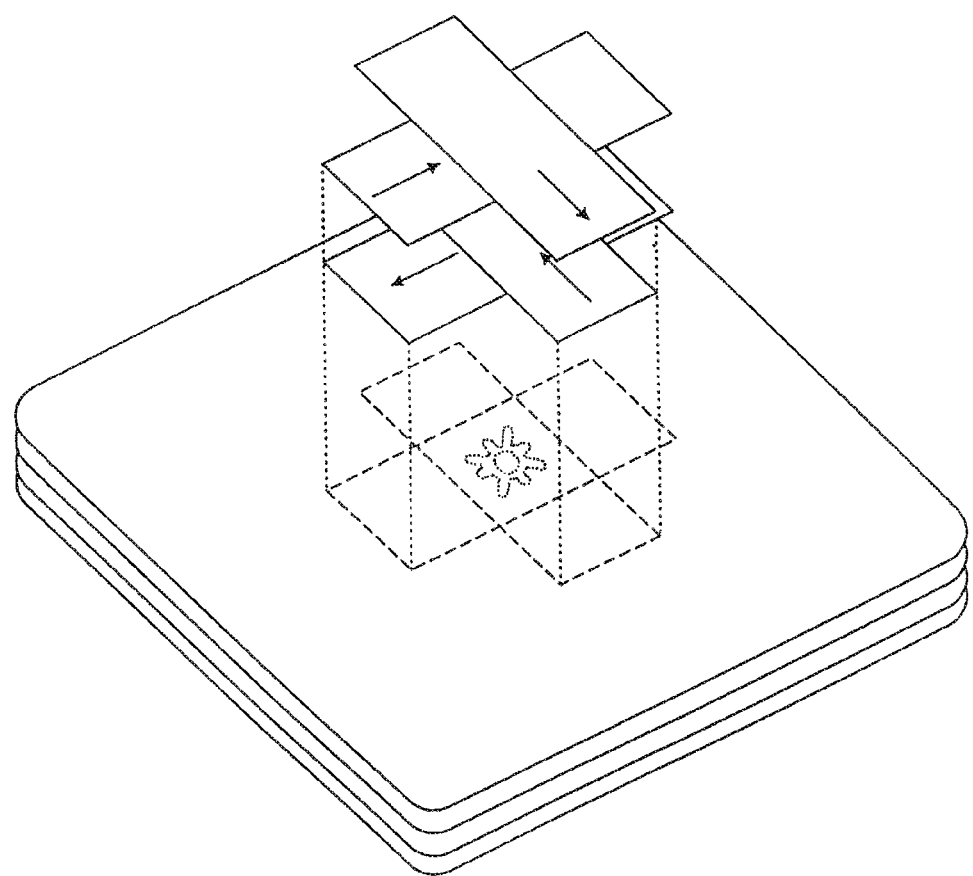
FIG. 11 illustrates a method of constructing the breachable barrier material in an embodiment of the present invention.

The breachable barrier material can be applied to the framework as a single layer or in multiple layers. When using multiple layers of breachable barrier material, it is preferred to orient the individual layers in different directions (see e.g. FIG. 11).

The framework is made of materials that are capable of supporting the breachable barrier material while the barrier material is fully covering the opening delimited by the framework. The materials of the framework permit the framework to be readily shaped, reshaped, or otherwise altered in configuration while the invention is located at an implantation site. The framework can be made of malleable materials, plastically deformable materials, and/or self-expanding (i.e., super-elastic) metals or polymers. When materials are used that do not lend themselves to visualization with fluoroscopy, x-ray imagining, magnetic resonance imaging, etc., radio-opaque or other imaging compounds can be introduced into the framework materials.

Figure 7A:
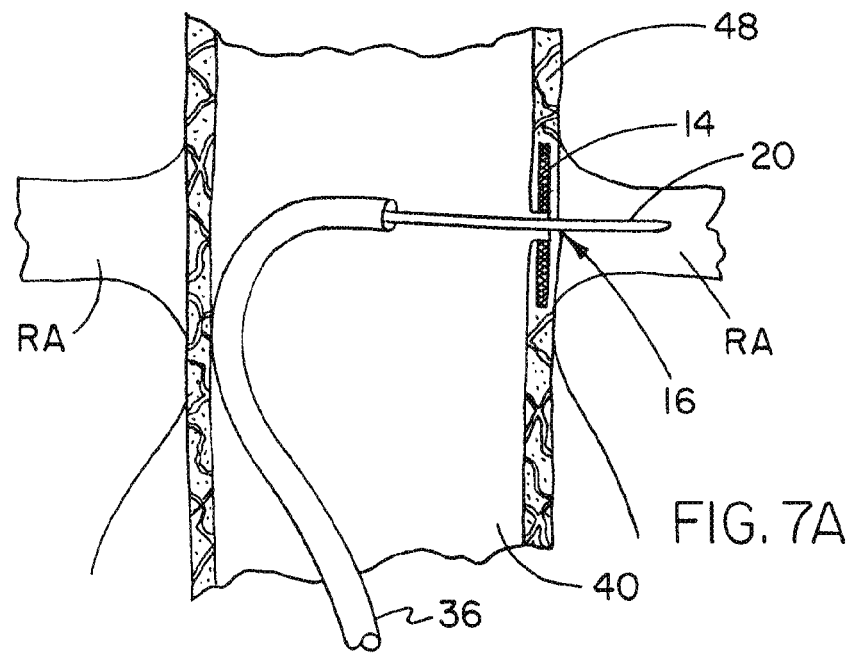
FIGS. 7A-7D illustrate the present invention being utilized to provide perfusion to side branches of a blood vessel.
Figure 7B:
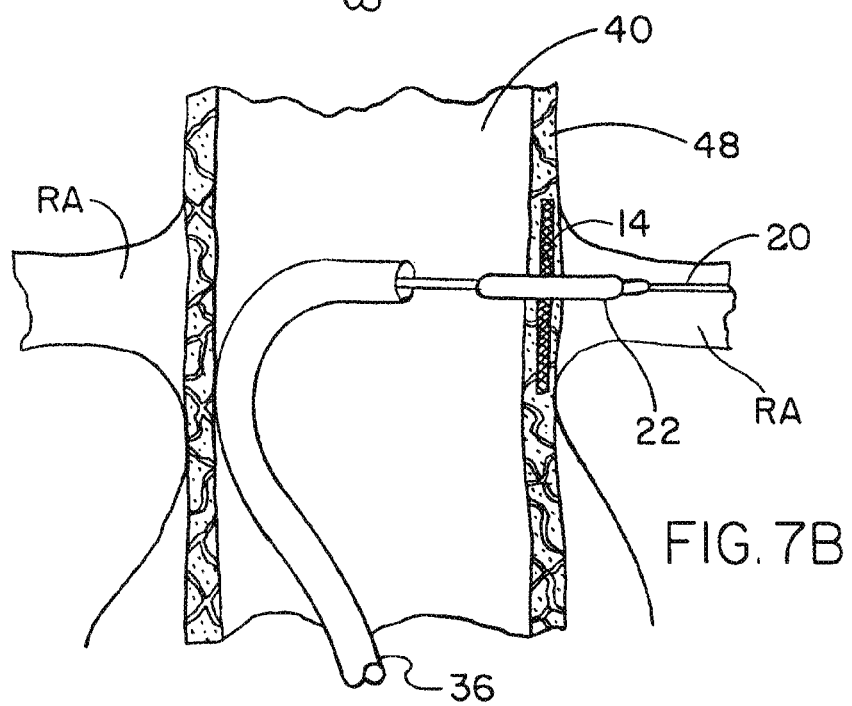
Figure 7C:
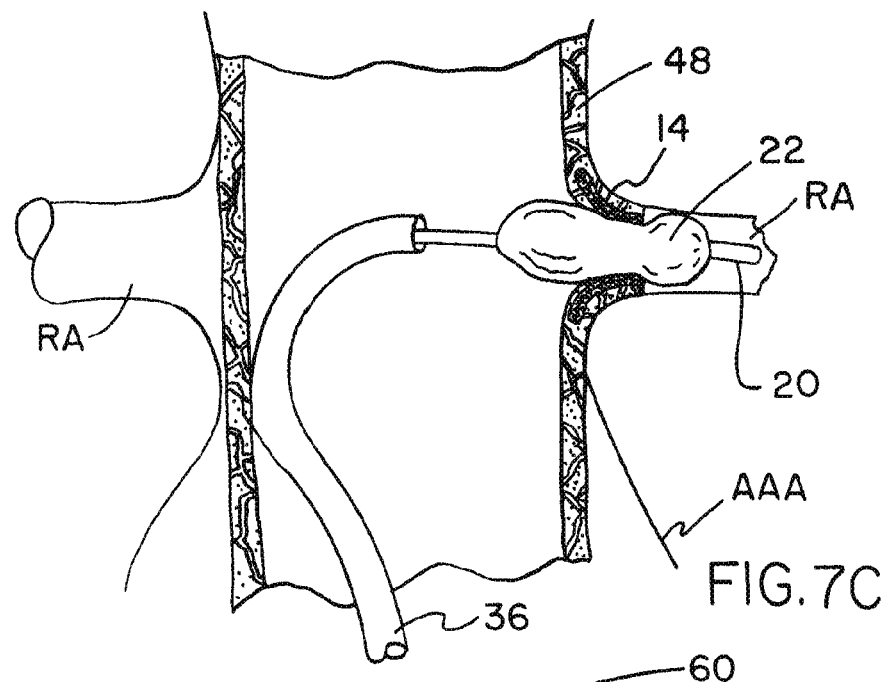
Figure 7D:
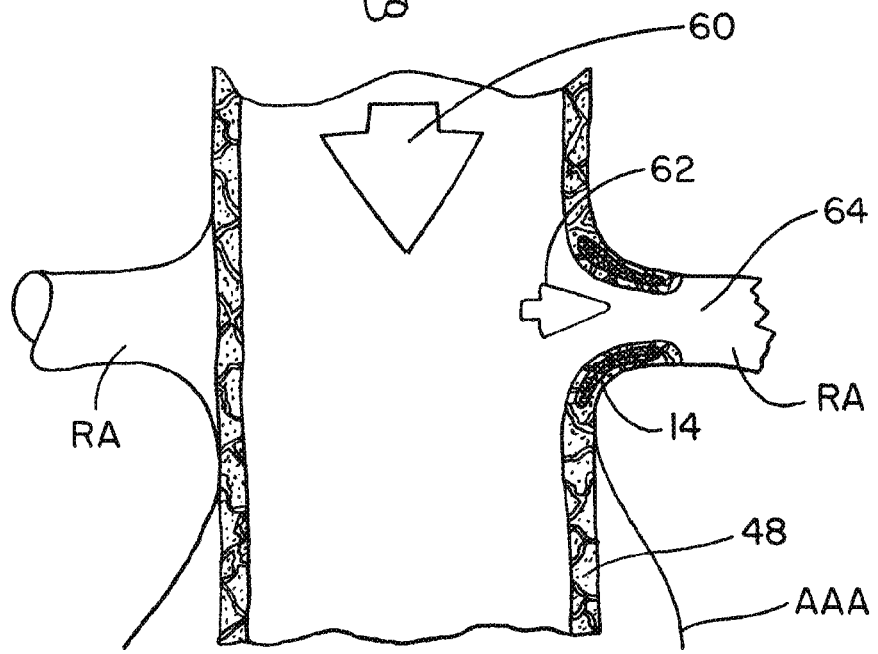
Figure 7E:
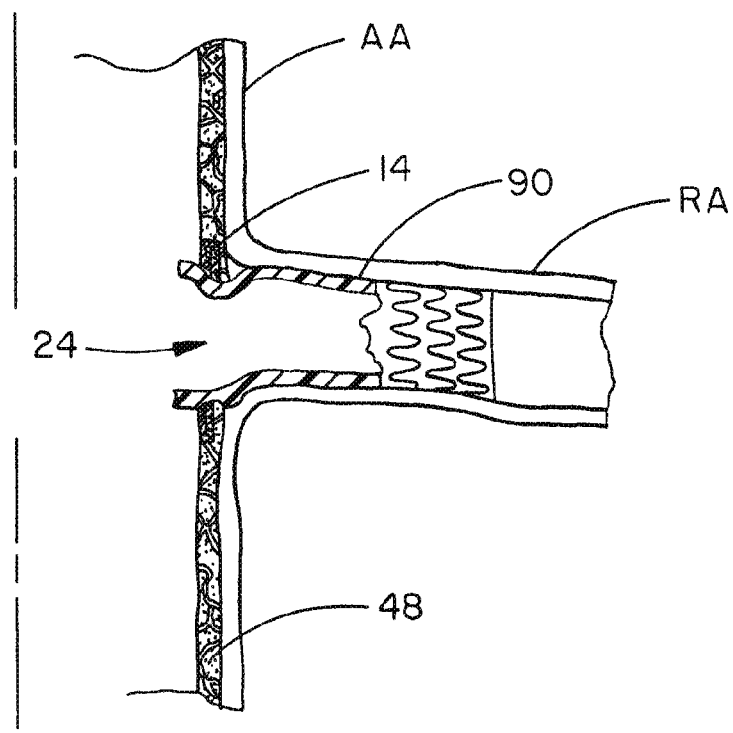
FIG. 7E illustrates an embodiment of the present invention serving as attachment means for another medical device.

The materials of the framework also need to be sufficiently resilient to provide permanent reinforcement of peripheral regions of the aperture under physiological conditions. In addition to providing structural support to peripheral regions of the aperture portion of the invention, the framework component can serve as anchoring means for other medical devices 90 attached thereto (e.g., FIG. 7E).

Suitable materials for the framework include, but are not limited to, implantable metals such as gold, silver, tantalum, tungsten, and chromium, implantable metal alloys such as stainless steel, nitinol metal, and implantable polymers such as polyurethanes, fluorinated ethylene propylene, and polytetrafluoroethylene. The framework can be made by molding, casting, laser cutting and/or laser machining, stamping, photo-etching, wire-forming, electrical discharge machining (EDM), bent wire techniques, or other suitable fabrication method.

In embodiments of the present invention that include a patch, tube, or other walled component, essentially any implantable material can be used for the component. Suitable materials include but are not limited to, implantable metals, implantable metal alloys, implantable polymers such as polyester (Dacron®), polyamide (Nylon), polytetrafluoroethylene, silicone, and polyurethane.

The present invention can be constructed in a variety of ways. The invention can be made by attaching the breachable barrier material to the framework material with adhesives, heat, pressure, and/or ultrasonic welding. In turn, the breachable barrier material can be attached to an implantable medical device with similar methodologies. The invention can also be incorporated into an implantable medical device by molding, sewing, wrapping with a film or membrane, and/or mechanical fixation.

An implantable medical device made of an expanded polytetrafluoroethylene (ePTFE) in the form of a tube or sheet can be supplied with an embodiment of the present invention by first cutting a hole in the ePTFE slightly smaller than the largest diameter of the framework component. Next, a powder coating of fluorinated ethylene propylene (FEP) is applied to both sides of the framework material and the framework material placed over the hole in the ePTFE material. A suitably sized piece of breachable barrier material is placed over the framework component. Heat and pressure are applied to the combination to attach the materials together.

Another method of attaching the present invention to an implantable medical device involves applying an adhesive material, such a room temperature vulcanizing (RTV) silicone, to both sides of the framework material and pressing one side of the framework onto a wall of the medical device having a suitably sized hole formed therein. A suitable breachable barrier material is then pressed onto the other adhesive-coated side of the framework component. Any excess barrier material is trimmed away from the framework to complete the installation.

Yet another method of attaching the present invention to an implantable medical device involves placing a framework component over a suitably sized hole in a wall of the medical device and wrapping one or more layers of a biocompatible film over the framework component. In this embodiment, the wrapped film layer(s) can also serve as the breachable barrier material. The film wrapping material can be further secured by heating the construction.

For implantable medical devices having a wall element in the form of a meshwork, the present invention can be attached to the medical device in such a way that the opening is accessibly through holes in the meshwork. In this embodiment, an adhesive-coated framework material is placed on a breachable barrier material. Additional adhesive is placed on perimeter regions of the barrier material. A meshwork device is placed over this combination so the opening of the present invention is accessible through one or more holes in the meshwork. Pressure is applied to the construct to adhere the components together. A preferred implantable medical device is a woven mesh material commercially available from Davol, Inc. under the trade name Bard® Marlex™ Mesh—Monofilament Knitted Polypropylene (Catalog No. 011265).

These construction methodologies are exemplary and are not intended to limit the scope of the present invention.

EXAMPLES

Without intending to limit the scope of the present invention, the apparatus and method of production of the present invention may be better understood by referring to the following examples.

Example 1

A planar sheet embodiment of the present invention, approximately 8.3 cm (3.25") by 13.3 cm (5.25"), was constructed as follows. A first layer of an expanded polytetrafluoroethylene (ePTFE) sheet material having a thickness of about 0.4 mm was obtained from the Medical Products Division of W.L. Gore & Associates, Inc., Flagstaff, Ariz. under the tradename GORE-TEX® Cardiovascular Patch as part number 1800610004 (FIG. 12, part A1).

Figure 12:
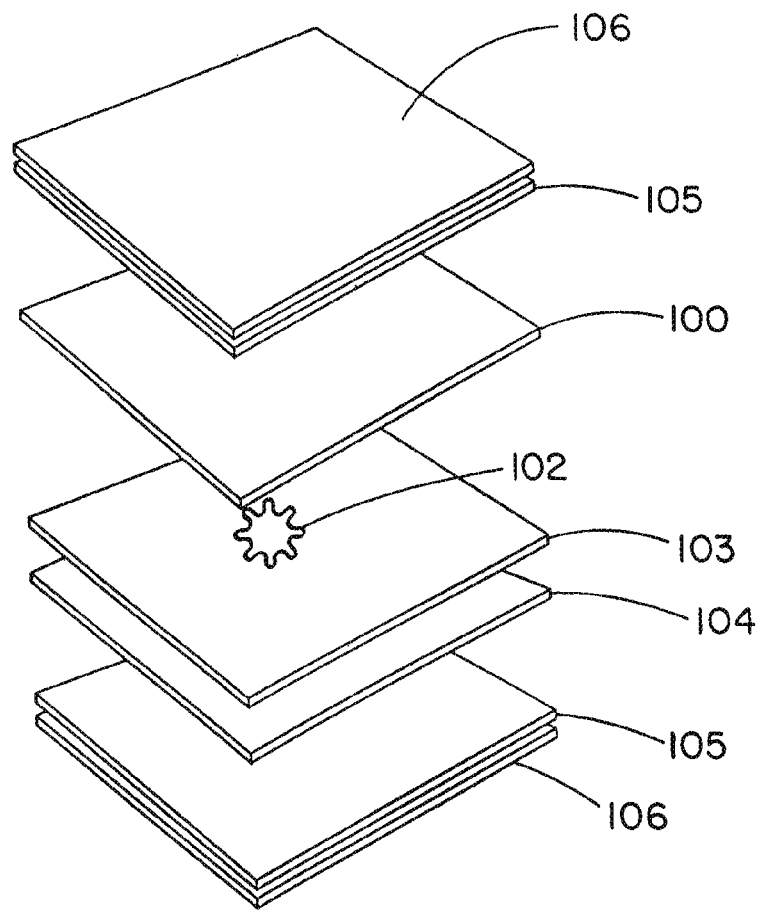
FIG. 12 is an exploded view of an embodiment of the present invention under construction.

A second layer of a fluoro-elastomeric sheet material composed of a thermoplastic copolymer of tetrafluoroethylene (TFE) and perfluoro(methyl vinyl ether) (PMVE) was constructed by compression molding the crumb form of the copolymer at a temperature of about 250° C. to form a sheet about 0.2 mm (0.008") in thickness (FIG. 12, part A3). The resulting material had the attributes described in TABLE 1 below.

A third layer of sheet material (FIG. 12, part A4) is composed of ePTFE made according to U.S. Pat. No. 4,482,516, issued to Gore. The sheet material was approximately 0.17 mm thick with an average fibril length of greater than about 10 microns.

A sheet of medical grade 316 stainless steel was obtained from Laserage Technologies, Inc., Waukegan, Ill. for use in constructing a framework. The framework was laser machined into an undulating pattern having a continuous, generally circular, ringed configuration (FIG. 12, part A2). The thickness of the framework was about 0.4 mm (0.016"). The minimum distance between individual framework elements located opposite one another in the opening delimited by the framework was about 0.2 mm (0.008").

These four components were aligned together as shown in FIG. 12. Components 100, 102, 103, and 104 were placed between layers of high temperature padding material and aluminum plates (FIG. 12, parts 105, 106). The aluminum plates were approximately 15.2 cm (6") square and 0.062" thick. The high temperature padding material 105 was made of GORE-TEX® Soft Tissue Patch having a thickness of about 2 mm (0.079") available from the Medical Products Division of W.L. Gore & Associates, Inc., Flagstaff, Ariz. as part number 1310015020. The assembly was placed in a heated Carver press and laminated together in the arrangement shown in FIG. 12 for about 5 minutes, at about 200°

C. with a pressure of about 0.5 Mpa (80 lb/in$^2$). Following the compression cycle in the press, the padding material was discarded.

Figure 13:
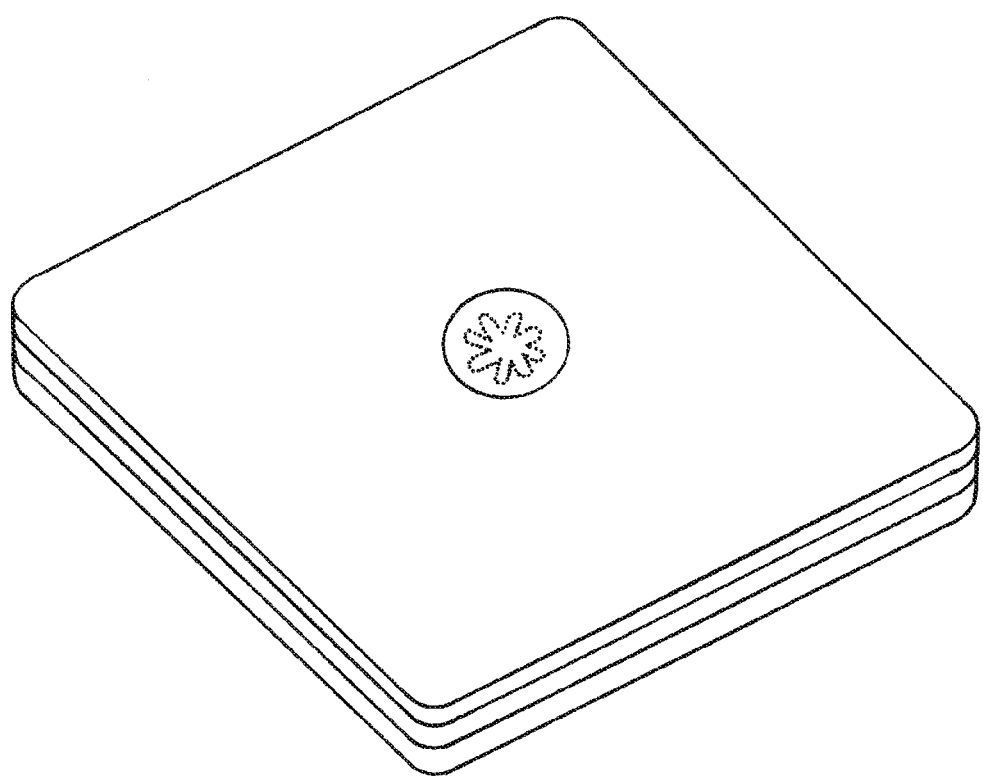
FIG. 13 is a perspective view of an embodiment of the present invention.

A 4 mm hole was then cut though all three layers of material at the center point of the reinforcement element using a 4 mm sharpened coring punch. Four layers of high strength ePTFE film made according to U.S. Pat. No. 5,476,589, issued to Bacino, were obtained and oriented at 90 degree angles with respect to one another (Figure C). A layer of discontinuous fluorinated ethylene propylene (FEP) coating was placed between each layer of ePTFE material. These combined materials were placed over the cutout hole and secured in place using a heated soldering iron applied around the outer perimeter of the cutout hole. Excess film material was than trimmed from the final assembly and the edges tacked down thoroughly with the heated soldering iron. The resulting article is shown in FIG. 13.

TABLE 1

| Characteristic | Target |
| --- | --- |
| PMVE wt % | about 60% |
| TFE wt % | About 40% |
| 100% Secant Modulus* | About 2.1-2.2 MPa |
| Softening Temperature | <275° C. |
| Thermal Degradation Temp. | >300° C. |
| Melt Flow Index** | >2.0 |
| Durometer | 60-80 Shore A |

*as per ASTM D412-98, using ½ scale Type IV dogbone with 250 mm/min crosshead speed and approximately 40 mm grip separation.
**grams per 10 minutes, 10 kg, 325° C.

Example 2

This example describes a tubular vascular graft having the article of Example 1 incorporated into the wall of the tubular graft. The article of Example 1 was trimmed and sewn into a corresponding hole cut through the wall of an ePTFE vascular graft. The ePTFE vascular graft was a GORE-TEX® Vascular Graft available from the Medical Products Division of W.L. Gore & Associates, Inc., Flagstaff, Ariz. as part number SA1604. The article from Example 1 was sewn into the corresponding hole of the tubular construct with an ePTFE suture material obtained from Medical Products Division of W.L. Gore & Associates, Inc. Flagstaff, Ariz. under the tradename GORE-TEX® Suture as part number CV-5. The resulting article is shown in FIG. 3B.

Accurate and illustrative examples of the invention have been described in detail however, it is readily foreseen that numerous modifications may be made to these examples.

We claim:

1. A medical device comprising:
a graft having a generally tubular shaped wall defining a luminal space for fluid flow therethrough, said wall comprising a frame with support elements, a first layer of a polymeric sheet material, and a second layer of polymeric sheet material;
a framework element disposed between said first layer and said second layer, wherein the support elements are separated from the framework element by the second layer of polymeric sheet material, and wherein a perimeter of the framework element only contacts said first layer and said second layer,
said framework element having an initial configuration whereby said perimeter incorporates peaks and valleys and delimiting a single, discrete, area fully covered with said first layer of polymeric sheet material forming polymeric breachable barrier material sufficient to at least partially bar liquids from crossing said material and have sufficient structural weakness to be readily structurally disrupted, and wherein said framework element has a second configuration, in which said peaks and valleys are permanently displaced radially outwardly to peripheral regions of an enlarged area, the enlarged area of the second configuration being larger than the single, discrete, area of the initial configuration, to form an enlarged permanent framed aperture in said enlarged area of said wall, wherein the permanent framed aperture extends through said wall, and said first and second polymeric sheet materials of said medical device.

2. The medical device of claim 1 wherein the medical device is an implantable medical device.

3. The implantable medical device of claim 2 wherein said medical device is a vascular prosthesis.

4. The implantable medical device of claim 3 wherein said vascular prosthesis is a vascular graft.

5. The implantable medical device of claim 3 wherein said vascular prosthesis is a stent-graft.

6. The implantable medical device of claim 3 wherein said vascular prosthesis is a surgical patch.

7. The implantable medical device of claim 1 wherein said breachable barrier material comprises a fluoropolymer.

8. The implantable medical device of claim 7 wherein said fluoropolymer is a polytetrafluoroethylene material.

9. The implantable medical device of claim 1 wherein said breachable barrier material comprises a bio-degradable material.

10. The implantable medical device of claim 1 wherein said breachable barrier material includes a filler material.

11. The implantable medical device of claim 1 wherein said breachable barrier material comprises an elastomer.

12. The implantable medical device of claim 1 wherein said framework element is made of an implantable metal.

13. The implantable medical device of claim 1 wherein said framework element is made of an implantable polymer.

14. The implantable medical device of claim 1 wherein the peaks and valleys form alternating concave and convex angles.

15. The medical device of claim 1 wherein the framework element is longitudinally displaced from the support elements.

16. An implantable medical device comprising a continuous wall including:
a meshwork forming holes,
at least one framework element in said wall defining an independent perimeter, the perimeter comprising a pattern of alternating peaks and valleys delimiting a single, discrete, area, the framework element delimiting an opening having a first area, and
a layer of a polymeric sheet material separating the meshwork from the framework element,
wherein the opening of the framework element is accessible through more than one of the holes in the meshwork, and
a breachable barrier material fully covering said opening, wherein a permanent aperture having a second area is formed following breach of said breachable material and said framework element is adaptable to be altered in shape and have a reinforced peripheral region in said continuous wall,
wherein the perimeter of the framework element only contacts said layer of polymeric sheet material and said breachable barrier material.

17. The implantable medical device of claim 16 wherein said continuous wall has a planar geometry.

18. The implantable medical device of claim 16 wherein said continuous wall has a tubular geometry.

19. The implantable medical device of claim 16 wherein said continuous wall is a vascular prosthesis.

20. The implantable medical device of claim 19 wherein said vascular prosthesis is a vascular graft.

21. The implantable medical device of claim 19 wherein said vascular prosthesis is a surgical patch.

22. The implantable medical device of claim 19 wherein said vascular prosthesis is a stent-graft.

23. The implantable medical device of claim 16 wherein said device is a component of a vascular prosthesis.

24. The implantable medical device of claim 23 wherein said vascular prosthesis is a stent-graft.

25. The implantable medical device of claim 16 wherein said continuous wall comprises a fluoropolymer.

26. The implantable medical device of claim 25 wherein said fluoropolymer is a polytetrafluoroethylene material.

27. The implantable medical device of claim 16 wherein said framework element is made of an implantable metal.

28. The implantable medical device of claim 16 wherein said breachable barrier material comprises a fluoropolymer.

29. The implantable medical device of claim 28 wherein said fluoropolymer is a polytetrafluoroethylene material.

30. The implantable medical device of claim 16 wherein said breachable barrier material comprises a bio-degradable material.

31. The implantable medical device of claim 16 wherein said breachable barrier material includes a filler material.

32. The implantable medical device of claim 16 wherein said breachable barrier material comprises an elastomer.

33. The implantable medical device of claim 16 wherein the peaks and valleys form alternating concave and convex angles.

34. The implantable medical device of claim 6 wherein said framework element is adaptable to be altered in shape such that the second area of the permanent aperture is larger than the first area of the opening.

35. The implantable medical device of claim 16 wherein the layer of polymeric sheet material is a second layer of polymeric sheet material, the wall further including a first layer of polymeric sheet material, wherein the meshwork is disposed between the first layer of polymeric sheet material and the second layer of polymeric sheet material.

36. A medical device comprising:
a graft having a generally tubular shaped wall defining a luminal space for fluid flow therethrough, said wall comprising a frame with support elements, a first layer of a polymeric sheet material, a second layer of polymeric sheet material, wherein the support elements are disposed between said first layer and said second layer;
a polymeric breachable barrier material;
a framework element separate from the support elements disposed between said second layer and said polymeric breachable barrier material,
wherein a perimeter of the framework element only contacts said second layer and said polymeric breachable barrier material,
said framework element having an initial configuration whereby said perimeter incorporates peaks and valleys and delimiting a single, discrete, area fully covered with said polymeric breachable barrier material, wherein said polymeric breachable barrier material is sufficient to at least partially bar liquids from crossing said material and have sufficient structural weakness to be readily structurally disrupted,
wherein said framework element has a second configuration, in which said peaks and valleys are permanently displaced radially outwardly to peripheral regions of an enlarged area, the enlarged area of the second configuration being larger than the single, discrete, area of the initial configuration, to form an enlarged permanent framed aperture in said enlarged area of said wall, wherein the permanent framed aperture extends through said wall, and said polymeric member of said medical device.

* * * * *